United States Patent [19]

Joly et al.

[11] Patent Number: 5,489,560
[45] Date of Patent: Feb. 6, 1996

[54] PROCESS FOR REGENERATING AN IMPURE CATALYST COMPRISING SULPHURIC ACID DEPOSITED ON SILICA

[75] Inventors: Jean-François Joly, Paris; Eric Benazzi, Montesson; Frédéric Chaigne, Valence; Jean-Yves Bernhard, Mennecy; Jean-Charles Viltard, Valence, all of France

[73] Assignee: Institut Francais du Petrole, Rueil Malmaison, France

[21] Appl. No.: 369,478

[22] Filed: Jan. 6, 1995

[30] Foreign Application Priority Data

Jan. 6, 1994 [FR] France .................................. 94 00144

[51] Int. Cl.⁶ .............................. C07C 2/58; C07C 2/62; B01J 20/34; B01J 38/12
[52] U.S. Cl. ............................ 502/38; 502/232; 585/730; 585/731
[58] Field of Search ..................... 502/38, 232; 585/730, 585/731

[56] References Cited

U.S. PATENT DOCUMENTS

| | | | |
|---|---|---|---|
| 2,813,835 | 11/1957 | Nozaki | 502/38 |
| 3,838,039 | 9/1972 | Ely et al. | 208/108 |
| 4,354,925 | 10/1982 | Schorfheide | 502/38 |
| 4,418,005 | 9/1983 | Dodd et al. | 502/217 |
| 4,822,760 | 4/1989 | Kashibe et al. | 502/38 |
| 5,321,149 | 6/1994 | Webb et al. | 502/38 |
| 5,336,833 | 8/1994 | Joly et al. | 585/731 |
| 5,362,694 | 11/1994 | Hollstein et al. | 502/38 |
| 5,420,093 | 5/1995 | Joly et al. | 502/216 |

FOREIGN PATENT DOCUMENTS

| | | | |
|---|---|---|---|
| 0346184 | 12/1989 | European Pat. Off. | 502/38 |
| 0539277 | 4/1993 | European Pat. Off. | |
| 9173136 | 10/1984 | Japan | 502/38 |
| 1164445 | 6/1989 | Japan | 502/38 |

Primary Examiner—Asok Pal
Attorney, Agent, or Firm—Millen, White, Zelano & Branigan

[57] ABSTRACT

The invention concerns a process for regenerating an impure catalyst comprising sulphuric acid deposited on silica.

It is characterized in that the catalyst is calcined at least once to eliminate organic hydrocarbon substances contained in the catalyst, in particular as a result of its use in aliphatic alkylation reactions.

19 Claims, No Drawings

PROCESS FOR REGENERATING AN IMPURE CATALYST COMPRISING SULPHURIC ACID DEPOSITED ON SILICA

The present invention concerns a novel process for eliminating organic hydrocarbon substances contained in an impure catalyst comprising sulphuric acid and silica which has been contaminated during chemical reactions in which the catalyst has participated. It also concerns the treatment of the gaseous effluent resulting from elimination of the organic hydrocarbon substances.

The present invention particularly concerns a process for the treatment of a used catalyst comprising silica and sulphuric acid-resulting from the catalytic alkylation of isobutane and/or isopentane by means of an olefin to produce at least one product from the group constituted by dimethylbutanes, trimethylpentanes, trimethylhexanes and trimethylheptanes, for example.

A variety of chemical and petrochemical processes use sulphuric acid as a catalyst. This acid is generally recycled for as long as the concentration of impurities, in particular organic impurities, allows this. The sulphuric acid which is purged is thus relatively concentrated in organic material which and is sent to a reprocessing plant. The only industrial reprocessing process for this discharged sulphuric acid is a process during which the acid is transformed into sulphur dioxide $SO_2$ by combustion, followed by transformation into sulphur trioxide ($SO_3$) which is then transformed back into sulphuric acid by absorption in water. Examples of processes which produce impure sulphuric acid, often called sulphuric sludge, are the synthesis of alcohols from ethylene hydrocarbons (in particular the synthesis of ethanol from ethylene, isopropanol from propylene and 2-butanol from a mixture of 1-butene and 2-butene), the alkylation of isobutane by olefins such as propylene or butenes and purification of hydrocarbons in refining operations.

These processes, in particular alkylation, produce relatively small amounts of used acid which are currently considered to be too small to be treated on site. The product is thus sent to sulphuric acid production plants where it is reprocessed into pure sulphuric acid and returned to the alkylation unit. Frequently, the treatment units for sulphuric sludge are a long way from the site where the sludge is produced, entraining numerous risks as regards transport, generally by road, of a product which is as dangerous and polluting as sulphuric sludge or the pure acid. This treatment comprises a first combustion step which transforms the acid into $SO_2$. In addition, the pure acid obtained is frequently more expensive than the fresh acid and the reprocessing plant will only reprocess if the supplier of the sludge takes back the pure acid, implying extra, non negligible costs for the alkylation plant.

A number of purification processes for used acid have been described. United States patent U.S. Pat. No. 3 652 708 describes a method for reducing the concentration of hydrocarbons in a residual acid by treatment with an excess of olefin before sending it to a combustion plant. This does not completely eliminate the problems mentioned above. The process described in European patent EP-B-0 052 548 uses nitric acid as an oxidizing agent for the organic hydrocarbon substances. This process involves treating the gases formed in a unit for eliminating nitrogen oxides, which represents an important drawback. The article by D E Shenfel'd et. al., in Zhurnal Prikaladnoi Khimii, Vol 61, No 7, pp 1550–1553, Jul. 1988, describes a treatment process for a used acid by decomposing the acid in two steps. During the first step, carried out at a temperature of between 50° C. and 270° C., a solid black residue is formed which resembles coke. This residue, with a weight which substantially corresponds to the carbon content of the initial used acid, is then oxidized in the presence of a stream of air at a temperature of more than 400° C. During the first step, conversion of the organic hydrocarbon raw materials present in the initial used acid, measured from the quantity of oxides of carbon formed by reaction with the sulphuric acid, is about 12%. The process described in this document has the major drawback of producing a solid carbon-containing residue which requires oxidation in air at a very high temperature. French patent application registration number 92/02072 describes agents with an oxidizing power which is greater than that of the sulphuric acid, which are introduced into the used acid to be treated. Examples of such oxidizing agents are $H_2O_2$, $H_2SO_5$ and $H_2S_2O_8$. The use of these agents makes the process complex and expensive.

The process of the present invention eliminates the problems associated with the techniques used in the processes of the prior art and provides a solution which can be readily installed at the location where the sulphuric sludge is produced, in particular an alkylation unit. This novel process is of particular interest for an isobutane alkylation process using olefins and a catalyst constituted by silica impregnated with sulphuric acid such as that described in French patent application registration number 91/13303.

The process of the present invention concerns a process for the elimination of organic hydrocarbon substances contained in this type of catalyst, i.e., comprising sulphuric acid on silica, said impure sulphuric acid at this stage generally containing about 50% to about 99.5% by weight of sulphuric acid and at least 0.1% by weight, expressed as the number of carbon atoms, of organic substances in their free or combined forms.

As indicated above, the silica impregnated with impure sulphuric acid may be an alkylation catalyst as described in French patent application registration number 91/13303 which has been purged from the alkylation unit for reprocessing.

By way of information, the average diameter of the catalyst particles is generally between 0.1 and 200 microns (1 micron=$10^{-6}$ m).

The treatment process for the impure acid contained in the pores of the silica comprises one or two steps. Depending on the chemical composition of the impure sulphuric acid to be treated, it can be effected in a single step.

In the first step, the catalyst, constituted by the silica impregnated with the impure acid, is calcined in a gas stream, for example a gas containing molecular oxygen, for example air or pure oxygen, at a flow rate of between 0.05 and 10 l/h/g of material to be treated, preferably between 0.1 and 5 l/h/g, at a temperature of between 100° C. and 400° C., preferably between 100° C. and 350° C., and more preferably between 170° C. and 330° C. The duration of the treatment is advantageously between a few minutes (for example, 3 minutes) and 8 hours.

In a second, optional, step, the solid obtained at the end of the first step is calcined in a gas stream, for example a gas containing molecular oxygen, for example air or pure oxygen, at a flow rate of between 0.05 and 10 l/h/g of material to be treated, at a temperature of between 400° C. and 600° C., preferably between 450° C. and 550° C., to eliminate the hydrocarbon deposits still present in the silica at the end of the first step.

The first and second calcining steps produce a gaseous phase containing the products formed by oxidation of the hydrocarbon compounds initially present in the impure sulphuric acid and by oxidation of sulphur dioxide $SO_2$, and a condensable liquid phase constituted by purified sulphuric acid.

We have discovered that, surprisingly, a large portion of the sulphuric acid contained in the silica is recovered in the first step: the sulphuric acid is then condensed from the vapor leaving the tube reactor in which the first calcining step of the invention is carried out. The condensed sulphuric acid is sufficiently pure for it to be used for the manufacture of an aliphatic alkylation catalyst, after mixing with an oleum such that the water content of the sulphuric acid solution thus prepared is less than about 2% by weight and after reimpregnation into the silica. In addition, the calcined silica leaving the second step of the process of the invention can be impregnated again with sulphuric acid to produce a new alkylation catalyst.

In the process of the invention, the gases formed during the second calcining step, in particular during the first part of the second step, are frequently not discharged directly into the atmosphere both in order to make use of the products they contain and because of legislation concerning environmental protection. These gases are most often reduced to transform the major portion of the oxides of sulphur therein into sulphur. When the process of the present invention is used in a refinery, it integrates easily into the refinery and the sulphur dioxide formed can be sent to a CLAUS unit (fume treatment) which is nearly always present in this environment, in which it is reduced to sulphur and may then be transformed back into sulphur trioxide by oxidation.

The following example illustrates the invention without limiting its scope.

EXAMPLE

Treatment of a used catalyst constituted by silica impregnated with sulphuric acid which has been tested in a pilot unit for alkylation of isobutane with olefins.

Composition of Fresh Alkylation Catalyst

The fresh alkylation catalyst was constituted by 41.7% by weight of a silica with an average particle diameter of 115 µm, and 58.3% by weight of anhydrous sulphuric acid.

Use of Catalyst for Isobutane Alkylation

A tube reactor with a diameter of 7 cm and a height of 15 cm was used to alkylate isobutane with 1-butene. The reactor, which contained 200 g of catalyst with the composition given above, was supplied at the bottom with a liquid phase with a linear velocity in the reactor of 0.36 cm/sec to ensure fluidization of the catalyst.

In order to simulate recycling of the isobutane from the isobutane/alkylate separation zone to the reactor inlet, a liquid mixture of isobutane and 1-butene containing 8.3% by weight of 1-butene was used as a feed.

The volume flow rate of the feed was 102 ml/h.

The major portion of the liquid effluent leaving the reactor was recycled to the reactor inlet after mixing with the feed. The recycle volume flow rate was 50 l/h. A liquid phase containing isobutane, unconverted 1-butene and the alkylate product was continuously extracted from the unit at a rate of close to 100 ml/h.

The temperature in the reactor was maintained at −3° C., and the pressure was 5 bar.

After 15 days of testing, the catalyst was discharged for regeneration using the process described in the present invention.

Regeneration of Used Catalyst 200 g of used catalyst in the form of a dry powder was calcined in a stream of 1.9 l/h/g of dry air, at a temperature of 290° C. for 5 hours. The gases were cooled and the condensed liquid was collected in a flask.

After calcining, a liquid fraction was recovered which had a weight of 87.54 g, along with a dry powder with a weight of 84.7 g. The weight of the non condensed gases was 27.76 g.

The recovered liquid contained about 93% by weight sulphuric acid, and the carbon-containing residue on the silica (about 1.1% by weight of carbon) could be completely eliminated by supplemental calcining in air at 550° C. for 4 hours.

The process of the invention recovered about 75% of the sulphuric acid initially present in the catalyst.

We claim:

1. A process for the purification of an alkylation catalyst of sulphuric acid deposited on silica, which contains at least 0.1% by weight, expressed as carbon atoms, of organic material in free or combined form as an impurity, which process comprises:

calcining said catalyst in a gas stream at a temperature of from 100° C. to 400° C. to remove at least a portion of the impurity.

2. The process of claim 1, wherein the catalyst, after the calcining, is subjected to a second calcining in a gas stream at a higher temperature of 400° C. to 600° C. to remove any of the impurity remaining in the catalyst.

3. The process of claim 2, wherein the second calcining is conducted after the initial calcining without intermediate steps.

4. The process of claim 1, wherein the catalyst is calcined at a temperature of 100° C. to 350° C.

5. The process of claim 1, wherein the catalyst is calcined at a temperature of 170° C. to 330° C.

6. The process of claim 1, wherein the calcining is conducted for from a few minutes to 8 hours.

7. The process of claim 2, wherein the second calcining is conducted at a temperature of 450° C. to 550° C.

8. The process of claim 1, wherein the gas stream is a gas containing molecular oxygen.

9. The process of claim 2, wherein the gas stream in each calcining step is a gas containing molecular oxygen.

10. The process of claim 1, which further comprises reducing the gas stream from the calcining to transform the sulphur oxides contained therein to sulphur.

11. The process of claim 2, which further comprises reducing the gas streams from both calcining steps to transform the sulphur oxides contained therein to sulphur.

12. The process of claim 1, wherein the catalyst, before purification, contains 50% to about 99.5% by weight of sulphuric acid.

13. The process of claim 1, wherein the gas stream is air or pure oxygen.

14. The process of claim 2, wherein the gas stream in each calcining step is air or pure oxygen.

15. The process of claim 1, wherein the gas stream is provided at a flow rate of 0.05 to 10 l/h/g of catalyst.

16. The process of claim 2, wherein the gas stream in each calcining step is provided at a flow rate of 0.05 to 10 l/h/g of catalyst.

17. The process of claim 1, which further comprises condensing the gas stream from the calcining to obtain a liquid sulphuric acid phase.

18. The process of claim 2, which further comprises condensing the gas streams from both calcining steps to obtain a liquid sulphuric acid phase.

19. The process of claim 2, which further comprises condensing the gas stream from the first calcining step to obtain a liquid sulphuric acid phase.

* * * * *